US012711610B2

(12) United States Patent
Rezaei et al.

(10) Patent No.: US 12,711,610 B2
(45) Date of Patent: Aug. 18, 2026

(54) SYSTEMS AND METHODS FOR PROCESSING OF FUNDUS IMAGES

(71) Applicants: Seyed Ehsan Vaghefi Rezaei, Auckland (NZ); David Squirrell, Auckland (NZ); Song Yang, Auckland (NZ)

(72) Inventors: Seyed Ehsan Vaghefi Rezaei, Auckland (NZ); David Squirrell, Auckland (NZ); Song Yang, Auckland (NZ)

( * ) Notice: Subject to any disclaimer, the term of this patent is extended or adjusted under 35 U.S.C. 154(b) by 319 days.

(21) Appl. No.: 17/645,927

(22) Filed: Dec. 23, 2021

(65) Prior Publication Data

US 2022/0207732 A1 Jun. 30, 2022

Related U.S. Application Data

(60) Provisional application No. 63/131,091, filed on Dec. 28, 2020.

(51) Int. Cl.
*G06T 7/00* (2017.01)
*A61B 5/00* (2006.01)
(Continued)

(52) U.S. Cl.
CPC ........ *G06T 7/0012* (2013.01); *A61B 5/14532* (2013.01); *A61B 5/4842* (2013.01);
(Continued)

(58) Field of Classification Search
CPC ..................... G06T 7/0012; G06T 7/70; G06T 2207/20081; G06T 2207/20084;
(Continued)

(56) References Cited

U.S. PATENT DOCUMENTS

2016/0081556 A1* 3/2016 Dreher ..................... A61B 3/10 600/407
2018/0260665 A1* 9/2018 Zhang ..................... G06F 18/22
(Continued)

FOREIGN PATENT DOCUMENTS

CN 107203778 * 9/2017
CN 110263755 * 9/2019
CN 111080630 * 4/2020

OTHER PUBLICATIONS

Vaghefi et al., "Detection of smoking status from retinal images; a Convolutional Neural Network study", Scientific Reports, (2019) 9:7180 (Year: 2019).*
(Continued)

*Primary Examiner* — Qian Yang
(74) *Attorney, Agent, or Firm* — Knobbe, Martens, Olson & Bear, LLP

(57) ABSTRACT

Methods and systems for detecting glycosylated haemoglobin (HbA1c) levels from at least one fundus image are disclosed. At least one fundus image associated with an individual is processed using a first set of one or more convolutional neural networks to determine a glycosylated haemoglobin (HbA1c) level for the at least one fundus image. Methods and systems of determining a risk level of progression of diabetic retinopathy of an individual are also disclosed. At least one fundus image associated with the individual is processed using a second set of one or more convolutional neural networks to determine a retinopathy grade for the at least one fundus image. A risk level of
(Continued)

progression of diabetic retinopathy of the individual is determined based on at least the HbA1c level and the retinopathy grade.

18 Claims, 3 Drawing Sheets

(51) Int. Cl.
*A61B 5/145* (2006.01)
*G06T 7/70* (2017.01)
*G06V 40/18* (2022.01)

(52) U.S. Cl.
CPC .......... *A61B 5/7267* (2013.01); *A61B 5/7275* (2013.01); *G06T 7/70* (2017.01); *G06V 40/197* (2022.01); *G06T 2207/20081* (2013.01); *G06T 2207/20084* (2013.01); *G06T 2207/30041* (2013.01); *G06T 2207/30168* (2013.01)

(58) Field of Classification Search
CPC . G06T 2207/30041; G06T 2207/30168; A61B 5/14532; A61B 5/4842; A61B 5/7267; A61B 5/7275; G06V 40/197; G06V 10/82; G06V 40/18; G06V 2201/03
See application file for complete search history.

(56) References Cited

U.S. PATENT DOCUMENTS

2018/0315193 A1* 11/2018 Paschalakis ............. A61B 3/12
2018/0336679 A1* 11/2018 Farchione ............... G06F 3/013
2021/0050089 A1* 2/2021 Mohammed ......... A61B 5/7267
2022/0207732 A1* 6/2022 Rezaei ................. A61B 5/4842

OTHER PUBLICATIONS

Gale et al., “Action on diabetic macular oedema: achieving optimal patient management in treating visual impairment due to diabetic eye disease”, Eye (2017) 31, S1-S20 (Year: 2017).*
Machine translation for CN 111080630 (Year: 2020).*
Machine translation for CN 107203778 (Year: 2017).*
Machine translation for CN 110263755 (Year: 2019).*

* cited by examiner 1000
1002
1004
1006
1008
1010
1012
1022
1030
1020-1
1020-1
1020-2

SYSTEMS AND METHODS FOR PROCESSING OF FUNDUS IMAGES

CROSS-REFERENCE TO RELATED APPLICATIONS

This application claims the benefit of priority under 35 U.S.C § 119(e) to U.S. Provisional Application No. 63/131,091, filed on Dec. 28, 2020, the disclosure of which is incorporated herein by reference in its entirety.

TECHNICAL FIELD

The present technology relates to systems and methods for processing fundus images, more particularly the processing of fundus images to determine glycosylated haemoglobin (HbA1c), and determining a risk level of progression of diabetic retinopathy of an individual.

BACKGROUND

Diabetes mellitus represents a group of chronic metabolic disorders affecting more than 451 million people worldwide. Diabetes is defined by increased levels of blood glucose which result in increased risk of microvascular and macro vascular complications. Both diabetes diagnosis and glycaemic control is clinically assessed using a laboratory measure of glycosylated haemoglobin (HbA1c), which reflects cumulative blood glucose history over the preceding two to three months. There is a strong evidence base that lowering HbA1c towards a normal range (e.g. less than 53 mmol/mol), reduces the diabetes vascular complication risk so is currently considered the test of choice for monitoring chronic management of diabetes. However measurement of HbA1c using blood tests only estimates blood sugar levels within a limited window in time immediately prior to the test, is invasive, and typically involves delays in the order of days before results are released.

The retina is the only organ that allows direct, non-invasive, in-vivo visualisation of the microvasculature and neural tissues. It thus affords a unique opportunity for the non-invasive detection of systemic vascular and neurological diseases. In recent decades, understanding of retina-systemic disease relationships has relied on classic epidemiological studies based on observable, human-defined retinal features (e.g., retinopathy or retinal vascular calibre).

Diabetic retinopathy is the leading cause of vision loss in the working age population, accounting for 2.6% of global blindness. It also has significant detrimental effect on patients' social and emotional welfare. It is now well recognised that screening for, and where appropriate treating, diabetic retinopathy can avoid sight loss, and thus reduce both the individual's disability and society's economic burden.

Worldwide, there are multiple studies that have examined the prevalence of diabetic retinopathy and its associated risk factors in large populations of people living with diabetes. These studies have shown that between 65-79% of patients at the initial diabetic retinopathy screening visit have no retinopathy, 18-35% of patients have non-sight threatening retinopathy, and 0.4-11% of patients have sight threatening retinopathy detected at initial screening assessment. Independent risk factors for retinopathy grade at initial screening assessment include: higher baseline HBA1c/fasting glucose levels, longer duration of diabetes treatment with insulin, ethnicity, age at diagnosis, type 1 diabetes, and higher diastolic blood pressure. Regardless of varying risk in different individuals, at present the rescreening frequency is typically fixed, between 12 to 18 months depending on jurisdiction and locality.

It is an object of the present disclosure to address at least one of the foregoing problems or at least to provide the public with a useful choice.

Further aspects and advantages of the present disclosure will become apparent from the ensuing description which is given by way of example only.

SUMMARY

According to one aspect of the present technology there is provided a method of detecting glycosylated haemoglobin (HbA1c) levels from at least one fundus image, the method performed by one or more processors, the method comprising: processing at least one fundus image associated with an individual using a first set of one or more convolutional neural networks to determine a glycosylated haemoglobin (HbA1c) level for the at least one fundus image.

According to one aspect of the present technology there is provided a system for detecting glycosylated haemoglobin (HbA1c) from at least one fundus image, the system comprising: a memory storing program instructions; a processor configured to execute program instructions stored in the memory and configured to: process at least one fundus image associated with an individual using a first set of one or more convolutional neural networks to determine a glycosylated haemoglobin (HbA1c) level for the at least one fundus image.

According to one aspect of the present technology there is provided a computer program product for detecting glycosylated haemoglobin (HbA1c) from at least one fundus image, the computer program product comprising: a non-transitory computer-readable medium having computer-readable program code stored thereon, the computer-readable program code comprising instructions that when executed by a processor, cause the processor to: process at least one fundus image associated with an individual using a set of one or more convolutional neural networks to determine a glycosylated haemoglobin (HbA1c) level for the at least one fundus image.

According to one aspect of the present technology there is provided a method of determining a risk level of progression of diabetic retinopathy of an individual, the method performed by one or more processors, the method comprising: processing the at least one fundus image using a first set of one or more convolutional neural networks to determine a glycosylated haemoglobin (HbA1c) level for the at least one fundus image; processing at least one fundus image associated with an individual using a second set of one or more convolutional neural networks to determine a retinopathy grade for the at least one fundus image; determining, based on at least the HbA1c level and the retinopathy grade, a risk level of progression of diabetic retinopathy of the individual.

According to one aspect of the present technology there is provided a system for of determining a risk level of progression of diabetic retinopathy of an individual, the system comprising: a memory storing program instructions; a processor configured to execute program instructions stored in the memory and configured to: process at least one fundus image associated with an individual using a first set of one or more convolutional neural networks to determine a glycosylated haemoglobin (HbA1c) level for at least one fundus image; process the at least one fundus image using a second set of one or more convolutional neural networks to determine a retinopathy grade for the at least one fundus image;

determine, based on at least the HbA1c level and the retinopathy grade, a risk level of progression of diabetic retinopathy of the individual.

According to one aspect of the present technology there is provided a computer program product for determining a risk level of progression of diabetic retinopathy of an individual, the computer program product comprising: a non-transitory computer-readable medium having computer-readable program code stored thereon, the computer-readable program code comprising instructions that when executed by a processor, cause the processor to: process at least one fundus image associated with an individual using a first set of one or more convolutional neural networks to determine a glycosylated haemoglobin (HbA1c) level for at least one fundus image; process the at least one fundus image using a second set of one or more convolutional neural networks to determine a retinopathy grade for the at least one fundus image; determine, based on at least the HbA1c level and the retinopathy grade, a risk level of progression of diabetic retinopathy of the individual.

In examples, the at least one fundus image may be processed using a third set of one or more convolutional neural networks to determine whether the at least one fundus image is of sufficient quality for further processing. In examples, processing using the third set of one or more convolutional neural networks is performed prior to processing using the first set of one or more convolutional neural networks. In examples, processing using the third set of one or more convolutional neural networks is performed prior to processing using the second set of one or more convolutional neural networks.

In examples the third set of one or more convolutional neural networks may be configured to classify the at least one fundus image as one of a plurality of categories, wherein at least a first one of the categories indicates the at least one fundus image is unsuitable for further processing using the first set of one or more convolutional neural networks, and a second one of the categories indicates the at least one fundus image is suitable for further processing using the first set of one or more convolutional neural networks. In examples, the plurality of categories may comprise a third category indicating the at least one fundus image should be reviewed by a clinician, but is unsuitable for further processing using the first set of one or more convolutional neural networks.

In examples, classifying the at least one image as unsuitable may comprise determining that the at least one fundus image is not directed to a relevant region of an eye of the individual. In examples, determining the at least one image is unsuitable may comprise determining that at least one property of the at least one fundus image is unsuitable. For example, the at least one fundus image may be determined as being over-saturated or underexposed.

In examples, a notification may be issued warning a user that the supplied images are unsuitable. This enables replacement images to be supplied.

In examples the at least one fundus image may be adjusted prior to processing using the first set of one or more convolutional neural networks. In examples, adjustment may be performed prior to processing using the second set of one or more convolutional neural networks. In examples, adjustment may be performed prior to processing using a fourth set of one or more convolutional neural networks to classify each of the fundus images according to orientation.

In examples, the image adjustment may be normalisation of the images, for example spatial or intensity normalisation.

In examples, a color balancing process may be performed on the at least one fundus image. In an example, a Gaussian filter may be applied to the at least one fundus image in order to perform color balancing. Image quality, as it pertains to color, can vary significantly between different fundus camera technologies and/or models. Colour balancing reduces the mismatch in images resulting from this, to assist with further processing.

In examples, a brightness adjustment process may be performed on the at least one fundus image. Image brightness can greatly vary due to environmental conditions (for example, lighting within a clinic) and patient pupil size. Brightness adjustment normalizes these variations to assist with further processing.

It is envisaged that adjusting the images may assist in reducing the computational load during processing by the one or more sets of convolutional neural networks.

In examples in which the at least one fundus image comprises a plurality of fundus images, the plurality of fundus images may be processed using a fourth set of one or more convolutional neural networks to classify each of the fundus images according to orientation. Reference to orientation of a fundus image should be understood to mean a classification of whether the image relates to a left-eye or a right-eye of an individual.

In examples the fourth set of one or more convolutional neural networks may be configured to group the fundus images according to the classification of left-eye or right-eye.

In examples the fourth set of one or more convolutional neural networks may be configured to group the fundus images according to at least one identifier. In examples the identifier may be one or more of: an identifier of the individual, or an identifier of image acquisition time.

In examples, the plurality of fundus images may be processed using the fourth set of one or more convolutional neural networks prior to processing using the first set of one or more convolutional neural networks. In examples, processing using the fourth set of one or more convolutional neural networks is performed prior to processing using the second set of one or more convolutional neural networks.

In examples, the plurality of fundus images may be processed using the fourth set of one or more convolutional neural networks following processing using the third set of one or more convolutional neural networks. It is envisaged that this may improve the accuracy of processing using the fourth set of one or more convolutional neural networks, and reduce the computational load. For completeness, alternative arrangements in which the plurality of fundus images may be processed using the fourth set of one or more convolutional neural networks before processing using the third set of one or more convolutional neural networks may be viable.

In examples, the functionality of one or more of the respective sets of one or more convolutional neural networks disclosed herein may be provided by a single set of one or more convolutional neural networks. In an examples, the functionality of the third of one or more convolutional neural networks and the fourth set of one or more convolutional neural networks may be provided by a single set of one or more convolutional neural networks.

A retinopathy grade provides a relative indication of neovascularization in the retina under two main classes: non-proliferative and proliferative. For example, the retinopathy grades may comprise: minimal non-proliferative, mild non-proliferative, moderate non-proliferative, severe non-proliferative, and proliferative. The second set of one or more convolutional neural networks may be configured to identify abnormalities in visual features in a fundus image (for example, but not limited to, microaneurysms, haemorrhages, and drusen). A grade may be based on one or more factors such as the type of abnormality, prevalence, and proximity to certain region(s) of the eye.

In examples, the second set of one or more convolutional neural networks may be configured to also determine a maculopathy grade for the at least one fundus image. Maculopathy should be understood as a subset of retinopathy, where the damaged tissue is at the proximity of the macula.

In examples, the second set of one or more convolutional neural networks may be trained on a plurality of training fundus images of individuals having a HbA1c of 40 mmol/mol or greater. Each training fundus image may comprise at least one image label comprising one or more of: a clinically triaged retinopathy grade, and a clinically triaged maculopathy grade.

In examples, the first set of one or more convolutional neural networks may be trained on a plurality of training fundus images of individuals having stable HbA1c levels over a predetermined period of time. For example, the predetermined period of time may be in the order of years—for example substantially two or more years, and more particularly at least four years. In an example, a HbA1c level associated with the training fundus images may be a mean HbA1c level of the training fundus images.

Reference to a risk level of progression of diabetic retinopathy should be understood to mean an indication of a relative likelihood of "time to event," where the event is progression of the retinopathy from a current grade to the next. The risk level of progression of diabetic retinopathy for the individual informs decision making by clinicians with regard to referral for retinal screening or treatment of the individual, or scheduling of rescreening.

In examples, the risk level may be determined for Type 1 diabetes mellitus (DM). In examples the risk level may be determined for Type 2 diabetes mellitus (DM). In examples the risk level may be determined for Type 1 and Type 2 diabetes mellitus (DM).

In examples, the risk level of progression of diabetic retinopathy may be determined using multivariate analysis. In examples, a regression model such as a nonlinear Cox proportional hazards model may be used to determine the risk level of progression of diabetic retinopathy.

In examples, determination of the risk level of progression of diabetic retinopathy may be performed based on a plurality of factors comprising two or more of: baseline grade, age, Hba1c level, duration of diabetes, ethnicity, and insulin use. In examples, the risk level determined for Type 1 diabetes mellitus (DM) may be based on at least: baseline grade, age, Hba1c level, and duration of diabetes. In examples, the risk level determined for Type 2 diabetes mellitus (DM) may be based on at least: baseline grade, ethnicity, insulin use, age, Hba1c level, and duration of diabetes. It should be appreciated that these exemplary factors are not intended to be limiting, and that other factors relating to one or more of the demographics, medical history, and/or lifestyle of the individual may be utilised in the determination.

In examples, the system may be configured to provide a recommendation for management of the individual's condition based on the determined risk level of progression of diabetic retinopathy. For example, a scale of risk levels may be provided, each risk level having an associated recommendation. In examples, a risk level indicating the individual as being healthy (as it pertains to retinopathy) may have an associated recommendation to discharge the individual without scheduling rescreening or intervention. In examples, one or more risk levels indicating the presence of disease but relatively low risk of progression may have an associated recommendation for scheduling rescreening. By way of example, a risk level indicating minimal disease and low progression risk may recommend rescreening in a longer term period (e.g. 18-24 months), a risk level indicating mild disease or risk of progression may recommend rescreening within a medium term period (e.g. 12-18 months), and a risk level indicating moderate disease or risk of progression may recommend rescreening in a shorter term period (e.g. 6 months). In examples, a risk level indicating relatively severe disease or risk of progression may recommend intervention or referral for same.

The above and other features will become apparent from the following description and the attached drawings.

BRIEF DESCRIPTION OF THE DRAWINGS

Further aspects of the present disclosure will become apparent from the following description which is given by way of example only and with reference to the accompanying drawings in which.

DETAILED DESCRIPTION

Figure 1:
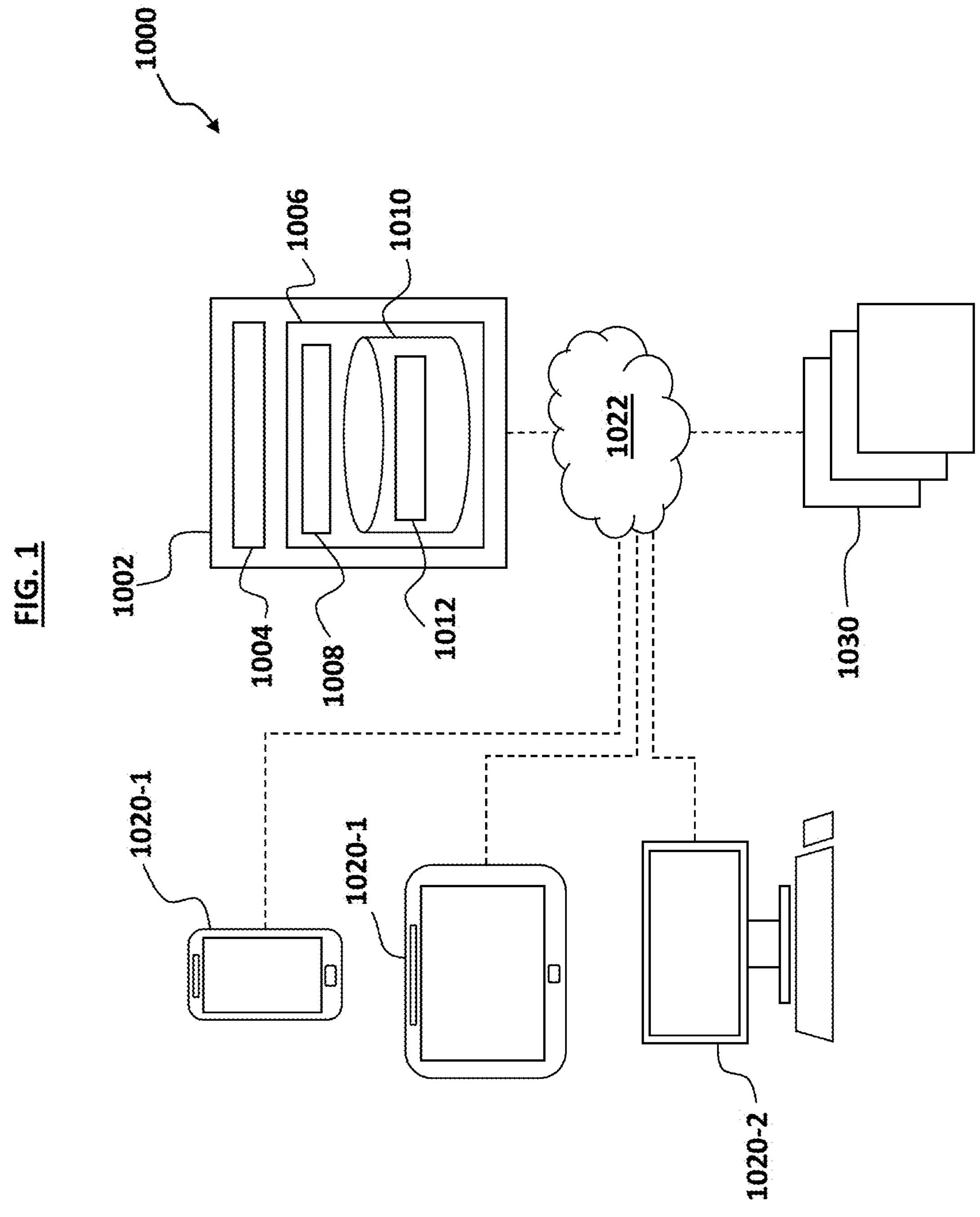
FIG. 1 is a schematic diagram of a system depicting various computing components that can be used alone or together in accordance with aspects of the present technology.

FIG. 1 presents a schematic diagram of a system 1000 depicting various computing components that can be used alone or together in accordance with aspects of the present technology. The system 1000 comprises a processing system 1002. By way of example, the processing system 1002 may have processing facilities represented by one or more processors 1004, memory 1006, and other components typically present in such computing environments. In the exemplary embodiment illustrated the memory 1006 stores information accessible by processor 1004, the information comprising instructions 1008 that may be executed by the processor 1004 and data 1010 that may be retrieved, manipulated or stored by the processor 1004. The memory 1006 may be of any suitable means known in the art, capable of storing information in a manner accessible by the processor, comprising a computer-readable medium, or other medium that stores data that may be read with the aid of an electronic device. The processor 1004 may be any suitable device known to a person skilled in the art. Although the processor 1004 and memory 1006 are illustrated as being within a single unit, it should be appreciated that this is not intended to be limiting, and that the functionality of each as herein described may be performed by multiple processors and memories, that may or may not be remote from each other.

The instructions 1008 may comprise any set of instructions suitable for execution by the processor 1004. For example, the instructions 1008 may be stored as computer code on the computer-readable medium. The instructions may be stored in any suitable computer language or format. Data 1010 may be retrieved, stored or modified by processor 1004 in accordance with the instructions 1008. The data 1010 may also be formatted in any suitable computer readable format. Again, while the data is illustrated as being contained at a single location, it should be appreciated that this is not intended to be limiting—the data may be stored in multiple memories or locations. The data 1010 may comprise databases 1012.

In some embodiments, one or more user devices 1020 (for example, a mobile communications capable device such as a smartphone 1020-1, tablet computer 1020-2, or personal computer 1020-3) may communicate with the processing system 1000 via a network 1022 to gain access to functionality and data of the processing system 1002. The network 1022 potentially comprises various configurations and protocols comprising the Internet, intranets, virtual private networks, wide area networks, local networks, private networks using communication protocols proprietary to one or more companies—whether wired or wireless, or a combination thereof. For example, fundus images obtained from one or more fundus imaging devices (herein referred to as a "fundus camera" 1030) may be input to the processing system 1002 via the user devices 1020.

A fundus camera typically comprises an image capturing device, which in use is held close to the exterior of the eye and which illuminates and photographs the retina to provide a 2D image of part of the interior of the eye. Many clinically important regions of the eye may be imaged, comprising the retina, macula, fovea, and optic disc. A single fundus image of a non-dilated eye captures less than 45° of the back of the eye. In practice, a clinician will often choose to capture several photographs while guiding the patients to look up, down, left and right, to create a larger field of view of the retina.

Figure 2:
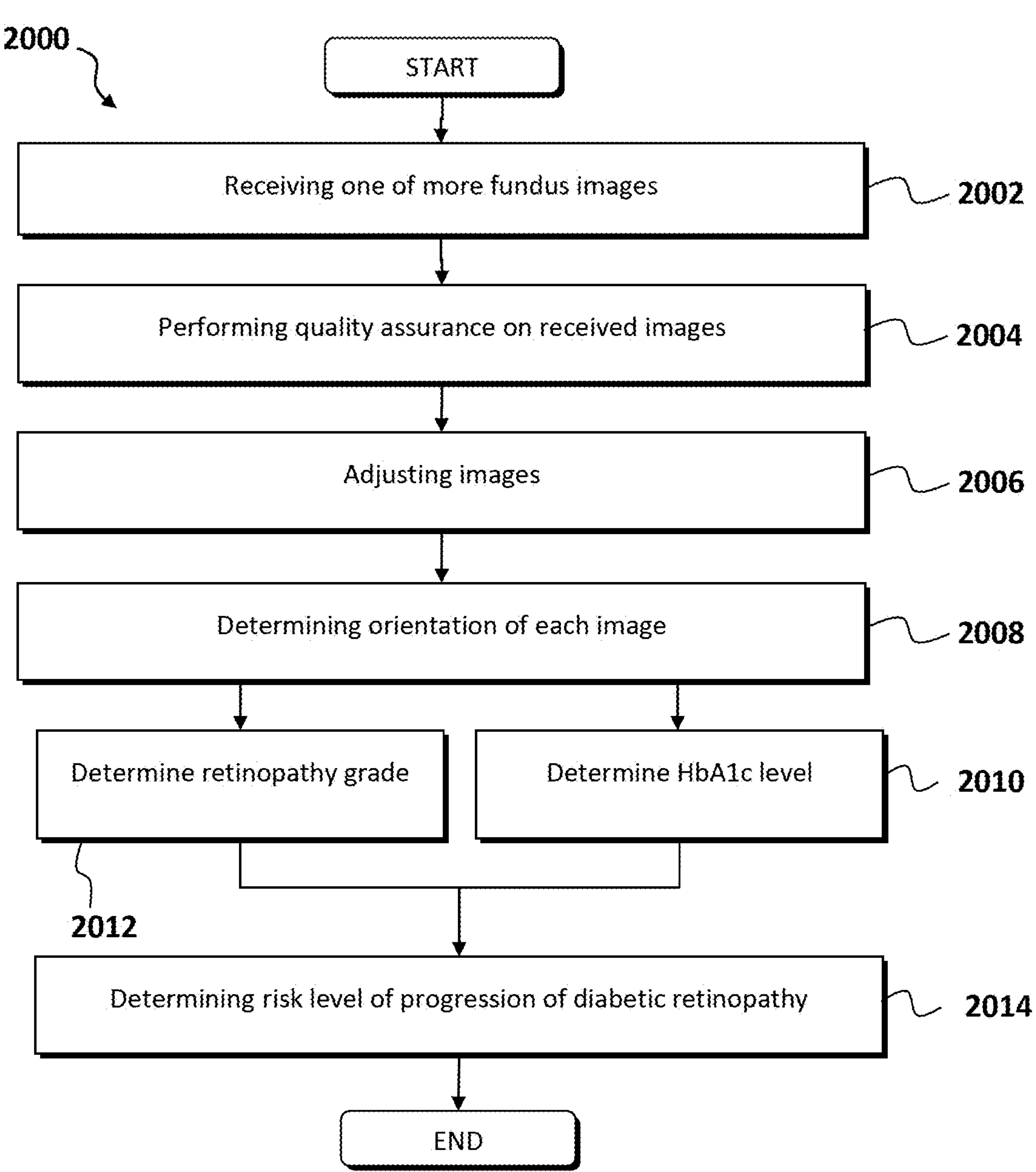
FIG. 2 is a flow diagram illustrating a method of processing fundus images in accordance with aspects of the present technology.
Figure 3:
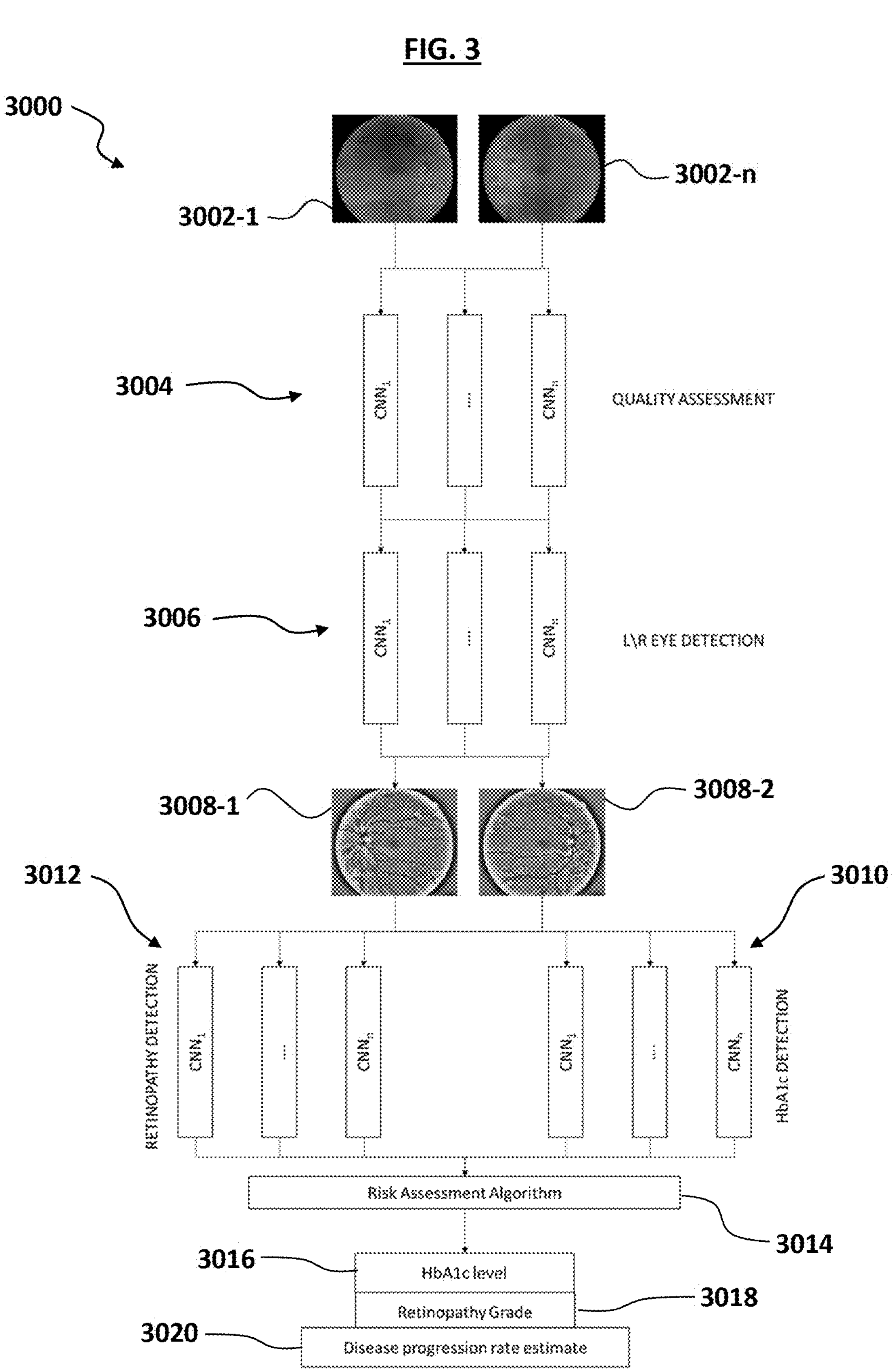
FIG. 3 is a diagram depicting various components and outputs of the method of processing fundus images in accordance with aspects of the present technology.

FIG. 2 illustrates a method 2000 of processing fundus images in accordance with aspects of the present technology. The method 2000 will also be described with reference to process architecture 3000 shown in FIG. 3. For completeness, it will be appreciated that the deep learning models and frameworks disclosed herein are provided by way of example, and that viable alternatives will be apparent to the skilled addressee.

The method 2000 utilises various convolutional neural networks ("CNN"). CNNs are deep learning architectures particularly suited to analysing visual imagery. A typical CNN architecture for image processing consists of a series of convolution layers, interspersed with pooling layers. The convolution layers apply filters, learned from training data, to small areas of the input image in order to detect increasingly more relevant image features. A pooling layer down-samples the output of a convolutional layer to reduce its dimensions. The output of a CNN may take different forms depending on the application, for example one or more probabilities or class labels.

In step 2002, one or more fundus images are received—for example a collection of fundus photographs 3002-1 to 3002-*n* of an individual. In step 2004, quality assurance is performed on the received images to confirm their suitability for further processing. In examples, the quality assurance is performed by a set of quality assurance ("QA") CNNs 3004.

The QA CNNs 3004 are trained by inputting sample images previously labelled by an expert clinician, and training them for sufficient iterations. In an example, a QA CNN 3004 was based on a modified XCEPTION design, and trained using a dataset of 20,000 images, wherein the dataset comprised similar proportions of four types of images: Type 1: Eyeballs, rooms or other irrelevant images; Type 2: Severely over-saturated or underexposed images; Type 3: Less than perfect images that could still be useful to a clinician in conducting a manual analysis; and Type 4: High quality images Experiments were run in an Intel Xeon Gold 6128 CPU @ 3.40 GHz with 16 GB of RAM memory and a NVIDIA GeForce TiTan V VOLTA 12 GB on Windows 10 Professional. Tensorflow 1.11.0 and Python 3.6.6 were utilised to implement the QA CNN 3004 models.

Hyperparameters comprised: (i) Batch Size: 64. Batch size refers to the number of training samples utilised in one step. The higher batch size, the more memory space need. For an input image size of 320*320, and GPU memory of 12 GB, the batch size was set at 64; (ii) Training \ validation \ testing split: (70 \ 15 \ 15); (iii) Epoch: 100. One epoch refers to one forward pass and one backward pass of all the training examples; (iv) Learning algorithms: the ADAM optimizer was utilised, being an advanced version of stochastic gradient descent; (v) Initial Learning Rate: 10e−3. Learning rate controls how much model adjusting the weights with respect the loss gradient. Typical learning rates are in the order of [10e−1, 10e−5]. In view of use of the ADAM optimizer and batch normalization, the initial learning rate was initially set at 10e−3; (vi) Loss Function: Softmax Cross Entropy; (vii) Dropout rate: 0.5.

The QA CNN 3004 described above achieved 99% accuracy in classifying an input image to the categories. Following training, all of the Type 1 and 2 images were removed. Type 3 images are shown to the clinician, but are not used in further processing. Type 4 images are used as part of further processing.

In step 2006, the fundus images may be adjusted before further processing—for example by performing brightness adjustment and color balancing for normalisation purposes.

In an example, a Gaussian filter may be applied to the original fundus photo. An example of such a filter may be expressed as:

$$I_c = \alpha I + \beta G(\rho) * I + \gamma$$

where * denotes the convolution operation, I denotes input image and G(p) represents the Gaussian filter with a standard deviation of ρ. While it will be appreciated that parameters may be optimised for each dataset, an exemplary set of parameters may comprise: alpha=4±1, beta=−4±1, gamma=128±50, ratio=10±10.

In step 2008, a determination is made as to the orientation of each image. Clinicians often obtain more than one image from a single eye, creating a larger view of the back of the eye. A set of orientation CNNs 3006 are trained to find similarities between several viewpoint images of the same eye and group them into a single image set. It is important to identify images that belong to the same eye, as a final clinical outcome may be the sum of analysis of each single image in that set.

An exemplary training environment for the orientation CNNs 3006 is similar to that described above for the QA CNNs 3004. A database of 160,585 images, from 75,469 eyes of 40,160 people was created. Each image was labelled with Left \ Right eye, patient ID (when available) and time stamp of image acquisition. The orientation CNNs 3006 were trained on this data set to identify the orientation (Left \ Right) of images, and group them based on ID \ acquisition time. The trained orientation CNNs 3006 achieved more than 99% accuracy. When implemented, the orientation CNNs 3006 group multiple images submitted by clinician into eye orientation and patient subgroups.

The resulting adjusted image sets 3008-1 and 3008-2, grouped by eye orientation, are then analysed. In step 2010, a determination is made as to HbA1c levels for the images 3008 using a set of HbA1c detection CNNs 3010.

In an example, a dataset of 2,123 patients, 7,727 eyes or 32,225 images was used for training and validation (with an 80/20 split), and a separate dataset of 1,779 patients, 5,847 eyes and 16,920 images was used for testing. These were patients identified as having stable HbA1c over several years, and the mean HbA1c was used as the ground truth for training and validation. The images were labelled by their HbA1c levels (measured in mmol/mol at the time of screening), none of which was less than 40 mmol\mol. This was a highly unbalanced dataset with a sharp peak (i.e. maximum prevalence) at 60 mmol/mol. Thus, the HbA1c was stratified according to [0, 40], [40, 60], [60, 80] and [80, 200] groups, and a random selection of 2000 images made from first three classes and all images with HbA1c higher than 80 retained.

The exemplary HbA1c detection CNN 3010 design was based on the EfficientNet-B3 model, and implemented based on TensorFlow 2 framework. Experiments were conducted on the following hardware environment: (CPU: Intel® Xeon® Gold 6128 CPU @ 3.40 GHz, GPU: NVIDIA Quadro RTX 8000). The batch size was set to be 6, with an objective of maximising utilisation of GPU memory in training. An ADAM optimizer was adopted with a learning rate 1*10e−3, with the objective of updating parameters towards a minimisation of the loss. Dropout is enabled with rate p=0.2, and the model was trained for at least 100 EPOCHs.

In this example, the classic mean squared error (MSE) for regression tasks was employed as the loss function, and the model performance was measured by mean absolute error (MAE), where:

$$MSE = \frac{1}{m}\sum_{i=1}^{m}(\hat{y}_i - y_i)^2$$

$$MAE = \frac{1}{m}\sum_{i=1}^{m}|\hat{y}_i - y_i|$$

The set of HbA1c detection CNN 3010 takes batch of images as an input, and outputs predicted HbA1c values for those images. For the model described above, the MAE dropped to 8 mmol\mol after 100 epochs of training. The model achieved MAE of 9.65 mmol\mol on the test dataset.

For completeness, it is noted that embodiments are contemplated in which the method 2000 is performed in order to obtain the predicted HbA1c values in isolation, i.e. without determination of the retinopathy grade and/or subsequent analysis to determine the patient risk of retinopathy progression, as described below.

In step 2012, a determination is made as to retinopathy and maculopathy grades (which may be referred to collectively as "retinopathy grades" for ease of understanding) for the images 3008 using a set of grading CNNs 3012.

In an example, the grading CNNs 3012 were based on a modified version of InceptionResnetV2 architecture. Training utilised 222,777 images from 112,616 eyes of 63,843 patient visits, all of these images being from individuals with HbA1c levels greater than 40 mmol/mol. The dataset was acquired from multiple eye clinics which use several different fundus camera models. Each image label comprised clinically triaged retinopathy and maculopathy grades by at least two retinal specialists. In case of disagreement, a resolution was sought from a third retinal specialist. The image labels were for retinopathy and maculopathy separately, with grades as: Minimal non-proliferative; Mild non-proliferative; Moderate non-proliferative; Severe non-proliferative; and Proliferative.

This dataset was split with a (70, 15, 15) ratio for training, validation and testing respectively. The fundus images were first cropped and resized to 800×800 pixel size. The batch size was set to be 6, with an objective of maximising utilisation of GPU memory in training. An ADAM optimizer was adopted with a learning rate 1*10e−3, with the objective of updating parameters towards a minimisation of the loss. Dropout is enabled with rate p=0.2, and the model was trained for at least 100 EPOCHs. Software was implemented by Python programming language under version 3.7, and adopted TensorFlow 2.0 and Keras frameworks because of the provision of automatic differentiation and backpropagation to update parameters. This grading CNNs 3012 achieved Accuracy of 98%, Sensitivity of 94% and Specificity of 96%.

Once the retinopathy grade and HbA1c levels are determined, the patient risk of retinopathy progression is determined in step 3014. More particularly, a determination is made as to the patient risk of retinopathy progression to a "referable" state—i.e. the risk of retinopathy progressing to a stage at which ongoing screening and/or intervention is recommended.

In examples, the patient risk of retinopathy progression is determined using regression analysis—for example utilising Cox proportional hazards analysis tables, examples of which are provided below.

TABLE 1

Cox proportional hazards analysis table for referable retinopathy and referable maculopathy for Type 1 diabetes mellitus (DM)

| | Referable Retinopathy Type 1 DM | | | Referable Maculopathy Type 1 DM | | |
|---|---|---|---|---|---|---|
| Contrast | Hazard Ratio | 95% Confidence Interval | P value | Hazard Ratio | 95% Confidence Interval | P value |
| Baseline grade 0 vs 1 | 1.455 | 0.875, 2.420 | 0.1487 | 1.917 | 1.399, 2.627 | <.0001 |
| Baseline grade 0 vs 2 | 32.44 | 15.55, 67.68 | <.0001 | 5.327 | 2.926, 9.697 | <.0001 |
| Age (Years) 45-64 | 0.309 | 0.147, 0.649 | 0.0019 | 0.702 | 0.493, 0.999 | 0.0494 |
| Age (Years) >= 65 | 1.266 | 0.484, 3.310 | 0.6300 | 0.567 | 0.273, 1.180 | 0.1293 |
| Hba1c (mmol) 65 to 75 | 1.887 | 0.837, 4.256 | 0.1258 | 1.020 | 0.701, 1.486 | 0.9166 |
| Hba1c (mmol) > 75 | 6.737 | 3.270, 3.88 | <.0001 | 2.132 | 1.524, 2.983 | <.0001 |

TABLE 1-continued

Cox proportional hazards analysis table for referable retinopathy and referable maculopathy for Type 1 diabetes mellitus (DM)

| | Referable Retinopathy Type 1 DM | | | Referable Maculopathy Type 1 DM | | |
|---|---|---|---|---|---|---|
| Contrast | Hazard Ratio | 95% Confidence Interval | P value | Hazard Ratio | 95% Confidence Interval | P value |
| Duration of diabetes (Years) 6-10 | 2.300 | 1.241, 4.261 | 0.0081 | 1.634 | 1.021, 2.617 | 0.0408 |
| Duration of diabetes (Years) 11 to 15 | 2.690 | 1.259, 5.747 | 0.0106 | 4.814 | 3.062, 7.568 | <.0001 |
| Duration of diabetes (Years) > 15 | 2.363 | 1.143, 4.886 | 0.0203 | 3.419 | 2.159, 5.415 | <.0001 |

This table is then converted to a hazard function denoted by T1(t) for retinopathy, which is estimated as below:

$$T1(t) = T1_{ret_0}(t) \times e^{(a_1x_1+a_2x_2+\ldots+a_nx_n)} + T1_{mac_0}(t) \times e^{(b_1x_1+b_2x_2+\ldots+b_nx_n)}$$

where $T1_{ret0}$ is the baseline retinopathy risk for Type 1 diabetes, $T1_{mac0}$ is the baseline maculopathy risk for Type 1 diabetes, $x_n$ is the nth row of the table, and $a_n$ & $b_n$ are associated retinopathy and maculopathy hazard ratios respectively.

TABLE 2

Cox proportional hazards analysis table for referable retinopathy and referable maculopathy for Type 2 diabetes mellitus (DM)

| | Referable Retinopathy Type 2 DM | | | Referable Maculopathy Type 2 DM | | |
|---|---|---|---|---|---|---|
| Baseline grade 0 vs 1 | 4.147 | 3.471, 4.955 | <.0001 | 3.414 | 3.104, 3.755 | <.0001 |
| Baseline grade 0 vs 2 | 31.30 | 23.78, 41.19 | <.0001 | 8.824 | 7.013, 11.10 | <.0001 |
| Ethnicity Maori vs NZ European | 1.311 | 0.653, 2.633 | 0.4462 | 0.946 | 0.610, 1.469 | 0.8057 |
| Ethnicity Polynesian vs Caucasian | 1.613 | 0.835, 3.116 | 0.1549 | 1.171 | 0.778, 1.763 | 0.4489 |
| Ethnicity Indian/South Asian vs Caucasian | 0.749 | 0.205, 2.732 | 0.6614 | 1.732 | 0.974, 3.079 | 0.0613 |
| Ethnicity Other Asian vs Caucasian | 1.085 | 0.559, 2.108 | 0.8094 | 1.526 | 1.035, 2.251 | 0.0329 |
| Ethnicity Other vs NZ European | 0.642 | 0.176, 2.341 | 0.5019 | 1.318 | 0.741, 2.344 | 0.3466 |
| Insulin Use | 1.091 | 0.901, 1.323 | 0.3723 | 1.238 | 1.096, 1.400 | 0.0006 |
| Age (Years) 45-64 | 0.572 | 0.473, 0.693 | <.0001 | 0.896 | 0.789, 1.017 | 0.0885 |
| Age (Years) >= 65 | 0.393 | 0.313, 0.495 | <.0001 | 0.582 | 0.503, 0.674 | <.0001 |
| Hba1c (mmol) 65 to 75 | 2.541 | 2.041, 3.163 | <.0001 | 2.050 | 1.830, 2.296 | <.0001 |
| Hba1c (mmol) > 75 | 6.896 | 5.786, 8.219 | <.0001 | 3.921 | 3.570, 4.307 | <.0001 |
| Duration of diabetes (Years) 6-10 | 1.744 | 1.479, 2.056 | <.0001 | 1.728 | 1.560, 1.903 | <.0001 |
| Duration of diabetes (Years) 11 to 15 | 2.277 | 1.858, 2.789 | <.0001 | 2.090 | 1.846, 2.365 | <.0001 |
| Duration of diabetes (Years) > 15 | 2.542 | 2.007, 3.218 | <.0001 | 2.269 | 1.958, 2.629 | <.0001 |

This table is then converted to a hazard function denoted by T2(t) for retinopathy, which is estimated as below $$T2(t) = T2_{ret_0}(t)\times e^{(a_1x_1+a_2x_2+\ldots+a_nx_n)} + T2_{mac_0}(t)\times e^{(b_1x_1+b_2x_2+\ldots+b_nx_n)}$$

where $T2_{ret0}$ is the baseline retinopathy risk for Type 2 diabetes, $T2_{mac0}$ is the baseline maculopathy risk for Type 2 diabetes, $x_n$ is the nth row of the table, and $a_n$ & $b_n$ are associated retinopathy and maculopathy hazard ratios respectively.

The determined HbA1c level(s) 3016, retinopathy grade(s) 3018, and patient risk of retinopathy progression 3020 may be output in various forms. For example, a report may be generated detailing one or more of these outputs for an individual.

In examples, the patient risk of retinopathy progression 3020 may have an associated recommendation for managing rescreening and/or intervention for the individual. For example, the patient risk of retinopathy progression 3020 may be determined on a scale, such as: (1) Patient healthy: recommend discharge without further action; (2) Minimal disease and low progression risk: recommend rescreening in 18-24 months; (3) Mild disease or risk of progression: recommend rescreening in 12-18 months; (4) Moderate disease or risk of progression: recommend rescreening in 6 months; (5) Severe disease or risk of progression: recommend immediate intervention.

Aspects of the present technology enable rapid and individualised determination of (1) HbA1c level, and/or (b) risk level of progression of diabetic retinopathy. The determination of HbA1c passed on fundus images is considered to represents a longer range of blood sugar level fluctuations (in the order of years, in contrast to 2-3 months for a blood test), which is considered more clinically relevant, while also being non-invasive and significantly faster than a laboratory blood test. The individualised determination of a risk level of progression of diabetic retinopathy enables decision making regarding ongoing management of the patient's needs to be targeted to the individual, rather than such decisions being population based, thereby increasing the likelihood of a positive outcome for the individual and more efficient use of health resources.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the field of endeavour in any country in the world.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The present disclosure may also be said broadly to consist in the parts, elements and features referred to or indicated in the specification of the application, individually or collectively, in any or all combinations of two or more of said parts, elements or features. Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the present disclosure and without diminishing its attendant advantages. It is therefore intended that such changes and modifications be included within the present disclosure as defined by the appended claims.

The invention claimed is:

1. A method of detecting glycosylated haemoglobin (HbA1c) levels from at least one fundus image, the method performed by one or more processors, the method comprising the following three steps in sequence:

(a) processing one or more fundus images associated with an individual using a first Quality Assurance (QA) set of one or more convolutional neural networks (CNNs) to determine whether the one or more fundus images are of sufficient quality for further processing;

(b) processing the one or more fundus images determined to be of sufficient quality for further processing using a second eye-identification set of one or more CNNs (eye-ID CNN), to identify the one or more fundus images belonging to a single eye; and (c) processing the one or more fundus images belonging to the single eye using a third glycosylated haemoglobin (HbA1c) set of one or more CNNs to determine an HbA1c level for the individual, wherein the first QA set of one or more CNNs, the second eye-identification set of one or more CNNs and the third glycosylated haemoglobin (HbA1c) set of one or more CNNs are computer-driven CNNs that have been previously trained over multiple iterations by a plurality of sample images previously labelled and quantified by an expert clinician, and previously validated using a plurality of test images from a plurality of test subjects, wherein the at least one fundus image is a two-dimensional visible-light photograph, and wherein an accuracy in determining the HbA1c level from the at least one fundus image is improved by using the combination of the three sets of the one or more CNNs compared to a determination made without using the three sets of the one or more CNNs.

2. The method of claim 1, further comprising the steps of:

processing the at least one fundus image associated with the individual using a fourth set of one or more convolutional neural networks to determine a retinopathy grade for the at least one fundus image; and determining, based on at least the HbA1c level and the retinopathy grade, a risk level of progression of diabetic retinopathy of the individual.

3. The method of claim 2, wherein the fourth set of one or more convolutional neural networks is configured to also determine a maculopathy grade for the at least one fundus image.

4. The method of claim 3, wherein the fourth set of one or more convolutional neural networks is trained on a plurality of training fundus images of individuals having a HbA1c of 40 mmol/mol or greater.

5. The method of claim 4, wherein each of the training fundus images comprise at least one image label comprising one or more of: a clinically triaged retinopathy grade, and a clinically triaged maculopathy grade.

6. The method of claim 2, wherein determination of the risk level of progression of diabetic retinopathy is performed based on a plurality of factors comprising two or more of: baseline grade, age, Hba1c level, duration of diabetes, ethnicity, and insulin use.

7. The method of claim 2, further comprising the step of providing a recommendation for management of the individual's condition based on the determined risk level of progression of diabetic retinopathy.

8. The method of claim 1, wherein the first QA set of one or more convolutional neural networks is configured to classify the at least one fundus image as one of a plurality of categories, wherein at least a first one of the categories indicates the at least one fundus image is unsuitable for further processing using the first QA set of one or more convolutional neural networks, and a second one of the categories indicates the at least one fundus image is suitable for further processing using the first set of one or more convolutional neural networks.

9. The method of claim 8, wherein the plurality of categories comprises a third category indicating the at least one fundus image should be reviewed by a clinician, but is unsuitable for further processing using the first set of one or more convolutional neural networks.

10. The method of claim 8, wherein classifying the at least one image as unsuitable comprises one or more of: determining that the at least one fundus image is not directed to a relevant region of an eye of the individual, and determining that at least one property of the at least one fundus image is unsuitable.

11. The method of claim 1, further comprising the step of performing image adjustment on the at least one fundus image prior to processing using the first set of one or more convolutional neural networks.

12. The method of claim 11, wherein the image adjustment is normalisation of the at least one fundus image.

13. The method of claim 1, wherein the at least one fundus image comprises a plurality of fundus images, and the method further comprises processing the plurality of fundus images using a fifth set of one or more convolutional neural networks to classify each of the fundus images according to orientation.

14. The method of claim 13, wherein the fifth set of one or more convolutional neural networks is configured to group the fundus images according to the classification of left-eye or right-eye.

15. The method of claim 13, wherein the fifth set of one or more convolutional neural networks is configured to group the fundus images according to at least one identifier.

16. The method of claim 1, wherein the first QA set of one or more convolutional neural networks is trained on a plurality of training fundus images of individuals having stable HbA1c levels over a predetermined period of time.

17. A system for detecting glycosylated haemoglobin (HbA1c) from at least one fundus image, the system comprising:

a memory storing program instructions;

a processor configured to execute program instructions stored in the memory and configured to:

process one or more fundus images associated with an individual using a first Quality Assurance (QA) set of one or more convolutional neural networks (CNNs) to determine whether the one or more fundus images are of sufficient quality for further processing;

process the one or more fundus images determined to be of sufficient quality for further processing using a second eye-identification set of one or more CNNs (eye-ID CNN), to identify the one or more fundus images belonging to a single eye; and process the one or more fundus images belonging to the single eye using a third glycosylated haemoglobin (HbA1c) set of one or more convolutional neural networks to determine an HbA1c level for the individual, wherein the at least one fundus image is a two-dimensional visible-light photograph.

18. The system as claimed in claim 17, wherein the processor is further configured to:

process the at least one fundus image using a fourth set of one or more convolutional neural networks to determine a retinopathy grade for the at least one fundus image; and determine, based on at least the HbA1c level and the retinopathy grade, a risk level of progression of diabetic retinopathy of the individual.

* * * * *